United States Patent [19]

Beach

[11] Plant 4,913

[45] Nov. 2, 1982

[54] SEEDLESS FRUITING MULBERRY

[75] Inventor: Carroll Beach, Ontario, Calif.

[73] Assignee: Armstrong Nurseries, Inc., Ontario, Calif.

[21] Appl. No.: 199,546

[22] Filed: Oct. 22, 1980

[51] Int. Cl.[3] ..... A01H 5/03

[52] U.S. Cl. ..... Plt./33

[58] Field of Search ..... Plt./33

*Primary Examiner*—Robert E. Bagwill

*Attorney, Agent, or Firm*—Synnestvedt & Lechner

[57] ABSTRACT

A new variety of fruiting mulberry tree, having a dense small growth habit and producing large, tender, juicy fruits, almost black in color, and almost free of seeds; bears from June 1 to August 25 in southern California; and fruit develops on current season's growth.

1 Drawing Figure

This invention relates to a new variety of fruiting mulberry tree of the *Morus migra* species (or a closely related species), which bears almost seedless fruit, which, at maturity, is almost black in color. It is a summer bearer, fruiting from about June 1 to about August 25, in southern California. Its hardiness has not yet been tested.

A large fruited mulberry tree, growing wild in a country of South America, attracted the notice of a friend of the inventor of the present variety. The friend imported one of the trees and planted it in a nursery in southern California. The fruit of the imported tree, and its habit of growth seemed even more desirable than the native stock. The inventor secured permission of the owner of the imported tree to plant some of its seeds. One of those seeds grew. A scion of that surviving seedling was grafted by the inventor, applicant herein, to root stock of the Hicks Mulberry, and it is the tree so produced which is the subject of the present description. The imported tree was destroyed when the land on which it was growing was sold, but the comparison comments below are based on observations made when the parent tree was still available. The major differences between the new variety and the imported tree rest, inter alia, on the fact that fruits of the present variety have a stronger and more vinous flavor, when fully ripe, and their skins are more tender. In addition, the new variety is almost seedless, whereas fruits of the imported tree have a somewhat larger complement of seeds than the tree claimed herein. The growth habit of the new variety is more compact and its foliage more dense than in the ancestral variety. The new variety produces fruits which are at least as large as those of the imported tree.

In comparison with other mulberry trees known in this region, which tend to provide small fruit (1" or less) over a period of about 4 to 6 weeks, this new mulberry produces notably larger fruit (1" to 2") which ripens over a substantially longer time period (approximately 10 weeks). The fruit of this new mulberry is seedless or nearly so, and the seeds which do form usually contain aborted embryos. Thus, unlike most other mulberries which produce viable seeds in their fruits which develop into often-unwanted new trees, this new cultivar generally does not produce new plantlets from seed. The tree itself is considerably more compact in its growth habit than most fruiting mulberries, and at maturity, is comparatively dwarf in ultimate height.

The accompanying drawings show, in full color, a pair of representative leaves of the new variety, and a fruit cluster, with leaves, in which may be seen the color changes as the fruit forms, grows and matures. In the description that follows, color designations beginning with small letters are used where the common term is aptly descriptive, whereas color designations beginning with capital letters are values taken from the Nickerson Colour Fan put out by Munsell Color Company.

TREE

The tree is of small to medium height for mulberries. It is upright-spreading in habit, usually growing somewhat wider than its height; a 30 year old tree being about 25 feet high and having a trunk of about 12 to 15 inches in diameter and a spread of about 30 feet. It is very dense and compact. Hardiness is as yet untested. It regularly produces very large crops of fruit.

Trunk: The tree is moderately stocky, with moderately rough bark.

Branches: The branches are also moderately stocky, with relatively short internodes and with some small corky lenticels. The color is between Strong Brown, 2.5 YR 4/7, and brownish gray.

New shoots: New shoots are moderately pubescent. Their color is between Moderate Yellowish Brown, 10 YR 4/4, and Strong Brown, 2.5 YR 4/7.

Leaves: The leaves are simple, broadly cordate and often with a cuspidate apex. They are moderately thick and leathery, semi-glossy on the upper surface and lightly pubescent on the undersurface. Their margins are coarsely serrate. The leaf size is from medium to large, ranging from about 4" to 5¾" in length and from about 3¾" to 6¾" in width. The leaf color on its upper surface is between Dark Yellowish Green, 10 GY 4/5, and Dark Yellowish Green, 2.5 G 3/3; on its lower surface it is between Moderate Yellowish Green, 5 GY 5/6, and Moderate Olive Green, 7.5 GY 4/4.

Flowers: The flowers are non-showy and of medium size. Light greenish yellow catkins appear, usually singly, at leaf axils after new growth breaks dormancy. This is generally in the months of April and May in Ontario, Calif.

FRUIT

The fruit is abundant. It develops on the current season's growth, and ripens from approximately June 1 to approximately August 25 in Ontario, Calif.

The size, when eating ripe (in mid-July in Ontario, Calif.) is from 1 to 2 inches in length and approximately ¾" in diameter irrespective of length.

The immature fruit is between pale yellowish green (a color value not present on the Nickerson Color Fan) and Pale Orange Yellow, 7.5YR9/4, varying through colors near Vivid Red, 5R5/13, and Dark Red, 2.5R3/7, as the fruit approaches maturity. The mature fruit is nearly black — significantly deeper than any color value found on the Nickerson Color Fan.

The shape is that of an oblong syncarp or fleshy compound fruit. The flower pistils persist on the ripe fruit as insignificant short, dry pubescent threads.

The receptacle is a long, narrow, stem-like organ, medium tender when eaten.

The skin is tender and translucent. The color appears the same as the flesh color.

The flesh is very juicy. The color gradually changes from a pale yellowish green through varying shades of red to nearly black as the fruit becomes eating ripe.

The seeds vary in number from a few to none at all. They are small, with a relatively soft seed coat practically undiscernable when the fruit is eaten. The few seeds that may develop in the fruits usually contain aborted embryos.

The flavor is tart-sweet and strong. It is somewhat vinous when black and fully ripe and is of good eating quality.

The keeping quality is poor, as a fresh fruit but excellent frozen, canned or in preserves.

The use is dessert, culinary and canning.

Its resistance to insects and diseases is good.

I claim:

1. A new and distinct variety of fruiting mulberry tree, substantially as herein illustrated and described, said variety being characterized in the large size and flavorful quality of its fruits, which are substantially seedless and of a blackish color when ripe, said tree ripening over a notably longer time span than most mulberries under parallel conditions, said tree being additionally characterized in its relatively compact and small habit of growth.

* * * * *

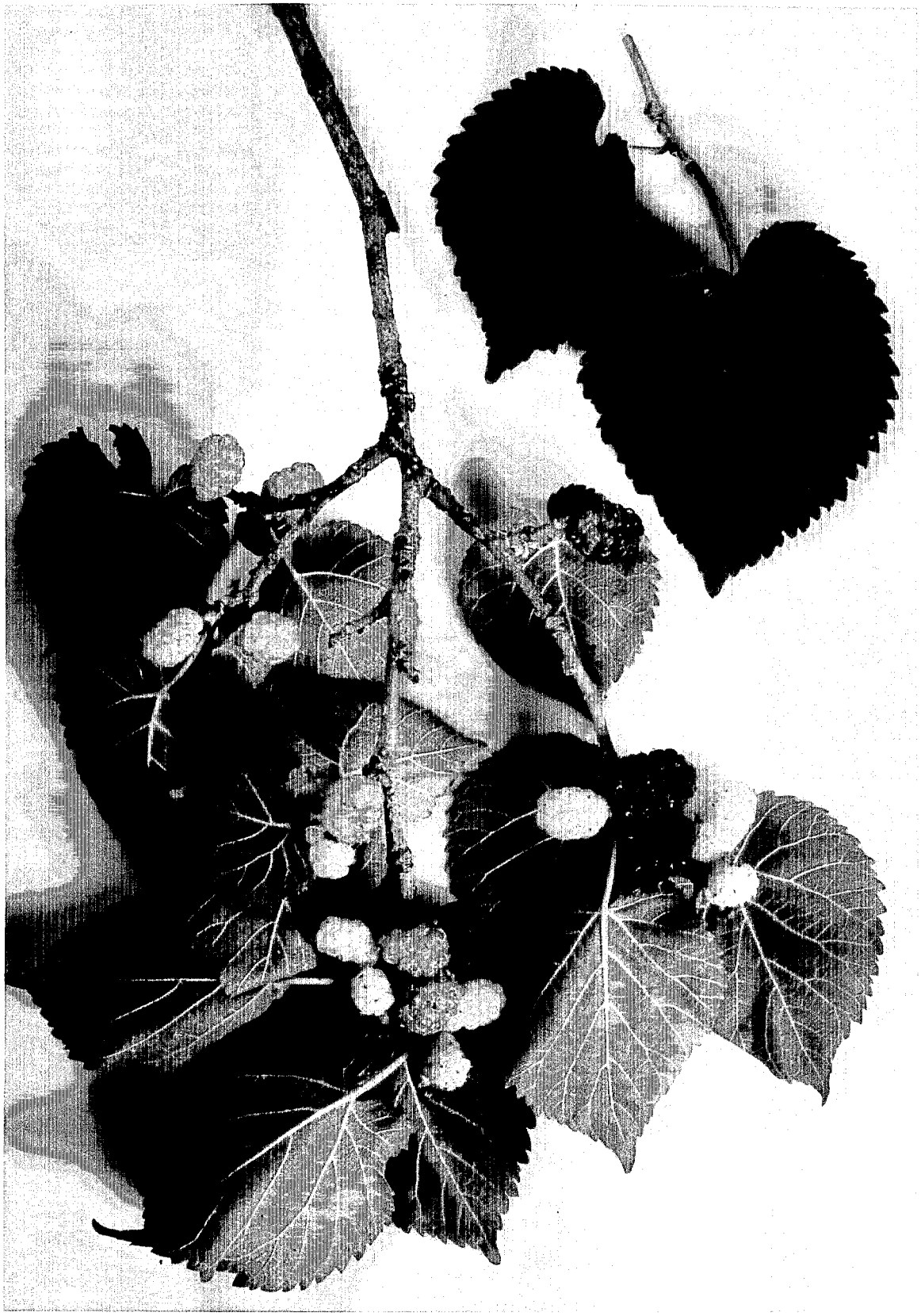

UNITED STATES PATENT AND TRADEMARK OFFICE

CERTIFICATE OF CORRECTION

PATENT NO. : PP 04,913

DATED : November 2, 1982

INVENTOR(S) : Carroll Beach

It is certified that error appears in the above—identified patent and that said Letters Patent is hereby corrected as shown below:

In Column 1, line 2, the word "migra" should read --nigra--.

Signed and Sealed this

*Eighth* Day of *February 1983*

[SEAL]

*Attest:*

GERALD J. MOSSINGHOFF

*Attesting Officer*

*Commissioner of Patents and Trademarks*